United States Patent [19]
Ujita et al.

[11] Patent Number: 5,981,811
[45] Date of Patent: Nov. 9, 1999

[54] PROCESS FOR PREPARING POLYPRENOLS

[75] Inventors: Katuji Ujita, Niigata-Pref.; Koichi Kanehira, New York; Yoshin Tamai, Niigata-Pref., all of Japan

[73] Assignee: Kuraray Co., Ltd., Kurashiki, Japan

[21] Appl. No.: 09/066,734

[22] Filed: Apr. 27, 1998

[30] Foreign Application Priority Data

Apr. 25, 1997 [JP] Japan ................................... 9-108687

[51] Int. Cl.$^6$ .................................................. C07C 33/02
[52] U.S. Cl. ........................ 568/875; 568/700; 568/714; 568/865; 514/724; 514/739
[58] Field of Search ..................... 568/700, 714, 568/865, 875; 514/724, 739

[56] References Cited

U.S. PATENT DOCUMENTS

| 4,839,389 | 6/1989 | Koyama et al. | 514/724 |
| 5,714,645 | 2/1998 | Asanuma et al. | 568/865 |

FOREIGN PATENT DOCUMENTS

| 2 122 610 | 1/1984 | United Kingdom . |
| 2 139 220 | 11/1984 | United Kingdom . |

OTHER PUBLICATIONS

N. Ya. Grigor Eva, et al, Bulletin of the Academy of Sciences of the USSR. Division of Chemical Science, vol. 35, No. 11, Part 1, pp. 2300–2306, "Reaction of Isoprenoid Olefins With $SeO_2$ in Aprotic Solvents", Nov. 1986.

Journal of the American Chemical Society; 92:14, Jul. 15, 1990, p. 4463.

Faulkner et al; "Application of the Claisen Rearrangement to Thesynthesis of Trans Trisubstituted Olefinic Bonds. Synthesis of Squalene and Insect Juvenile Hormone", Journal of the American Chemical Society/95:2/Jan. 24, 1973, pp. 553–563.

Okano et al., "Counter" Phase Transfer Catalysis of Water–Soluble Phosphine Complexes. Catalyitic Reduction of Allyl Chlorides and Acetates with Sodium Formate in Two–Phase Systems ; The Chemical Society of Japan; Chemistry Letters, pp. 1463–1466 (1986).

Hutzinger et al, "Stereospecific Reduction and Cross–Coupling of γ–Monosubstituted Llylic Chlorides Using Coordinatively Unsaturated Palladium Catalysts", J. Org. Chem. 1991, 56, 2916–2920.

*Primary Examiner*—James O. Wilson
*Assistant Examiner*—Howard Owens
*Attorney, Agent, or Firm*—Oblon, Spivak, McClelland, Maier & Neustadt, P.C.

[57] ABSTRACT

A process for the preparation of a polyprenol represented by formula (1):

where Y and Z individually represent a hydrogen atom or are coupled together to form a carbon-carbon bond; R represents a hydrogen atom or a protective group for a hydroxyl group, and n is 0 or an integer not less than 1, by reacting an organic complex of an alkali metal with a compound represented by formula (2):

where either V represents a halogen atom, while W and X are coupled together to form a carbon-carbon bond, or X represents a halogen atom, while V and W are coupled together to form a carbon-carbon bond; A represents a protective group for a hydroxyl group, and Y, Z and n are as defined above.

17 Claims, No Drawings

PROCESS FOR PREPARING POLYPRENOLS

BACKGROUND OF THE INVENTION

1. Field of the Invention

The present invention relates to a process for preparing polyprenols. The polyprenols prepared by the present invention are useful as pharmaceuticals or synthesis intermediates therefor. Among the polyprenols prepared by the present invention, is, for example, 3,7,11,15,19,23,27-heptamethyl-6,10,14,18,22,26-octacosahexaen-1-ol.

2. Description of the Related Art

Several methods are known for reducing an allylic terminal, including:

(1) using $NaBH_4$ in dimethylsulfoxide as a solvent [see J. Am. Chem. Soc., 92, 4463 (1970)], (2) using $LiAlH_4$ [see J. Am. Chem. Soc., 95, 553 (1973)], (3) using sodium formate as a hydrogen source in the presence of a palladium catalyst [see Chem. Lett., 1463 (1986)], and (4) using diisobutyl aluminum hydride (DIBAL) as a hydrogen source in the presence of a palladium catalyst [see J. Org. Chem., 56, 2918 (1991)].

In the case of the synthesis of a polyprenol from a terminal allyl halide, it is necessary not only to conduct dehalogenation but also to form a carbon-carbon double bond at a selected position. Upon dehalogenation of a terminal allyl halide, use of method (1) described above, however, causes hydroboration owing to $BH_3$ formed after dehalogenation. The more carbon-carbon double bonds present in the molecule, the more eminent such a tendency becomes, which brings about a reduction in the yield of a polyprenol. In the above-described method (2), on the other hand, it is difficult from an industrial viewpoint to handle $LiAlH_4$ because it is a powder and has undesirable ignition properties. The above-described method (3) involves a problem in selectivity because many positional isomers of the carbon-carbon double bond may be formed. Method (4) described above has high positional selectivity for a carbon-carbon double bond, but requires temperature as low as $-78°$ C. as necessary for the reaction and, in addition, the palladium catalyst is expensive.

Accordingly, any one of the above methods are not satisfactory for the preparation of a polyprenol selectively and industrially advantageously.

SUMMARY OF THE INVENTION

An object of the present invention is to provide a process for preparing a polyprenol selectively and in industrially useful yields by dehalogenating a terminal allyl halide, thereby forming a carbon-carbon double bond at a selected position.

In one aspect of the present invention, there is thus provided a process for preparing a polyprenol (hereafter abbreviated Polyprenol (1)) represented by the following formula (1):

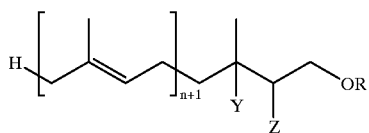

(1)

where

Y and Z each represent a hydrogen atom, or are coupled together to form a carbon-carbon bond;

R represents a hydrogen atom or a protective group for a hydroxyl group; and n is 0 or an integer not less than 1, which comprises reacting an organic complex of an alkali metal with a compound (hereafter abbreviated as Compound (2)) represented by the following formula (2):

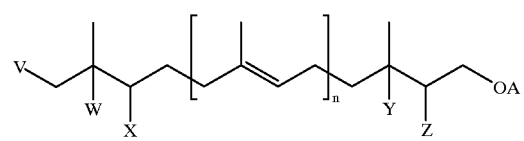

(2)

where either

V represents a halogen atom, while W and X are coupled together to form a carbon-carbon bond, or X represents a halogen atom, while V and W are coupled together to form a carbon-carbon bond;

A represents a hydroxyl protecting group; and

Y, Z and n have the same meanings as defined above with respect to formula (1).

A more complete appreciation of the invention and many of the attendant advantages thereof will be readily obtained as the same becomes better understood by reference to the following detailed description.

DETAILED DESCRIPTION OF THE PREFERRED EMBODIMENTS

In the above formula, no particular limitation is imposed on the protective group for a hydroxyl group represented by A and/or R, insofar as it is used for the purpose of protecting an alcohol. Examples of the protective group include acyl groups such as acetyl, butyryl, benzoyl and p-methoxybenzoyl; 1-alkoxyalkyl groups such as methoxymethyl, 1-ethoxyethyl and tetrahydropyranyl; aralkyl groups such as benzyl and p-methoxybenzyl; and tri-substituted silyl groups such as trimethylsilyl. Other suitable hydroxyl protecting groups are disclosed in *Protective Groups in Organic Synthesis*, Green and Wuts, Eds, 1991, incorporated herein by reference. Examples of the halogen atom represented by V or X include chlorine, bromine and iodine.

Examples of the alkali metal forming the organic complex of an alkali metal used in the present process include lithium and sodium. As a compound which forms the organic complex with the above-exemplified alkali metal, polycyclic aromatic compounds, such as naphthalene, methyl naphthalene, anthracene and biphenyl are preferred. The polycyclic aromatic compound may have 10 to 20 carbon atoms. From the viewpoint of economy and handling ease, it is preferable to use sodium as the alkali metal and naphthalene as the compound for forming the organic complex with the alkali metal.

In formula (1) and (2), n is 0 or an integer having a value greater than or equal to 1. The variable n may be, for example, 1, 2, 3, 4, 5, 6, 7, 8, 9, or 10. Preferably, n is 0 to 7, more preferably, 0 to 5.

The alkali metal is preferably used in an amount falling within a range of from 2 to 20 mole equivalents based on Compound (2), with a range of from 2 to 10 mole equivalents being more preferred. These ranges include all specific values and subranges therebetween, including 3, 5, 7, 10 and 15 mole equivalents. The compound which forms an organic complex with the alkali metal is preferably used in an amount falling within a range of 2 to 20 mole equivalents based on Compound (2), with a range of 5 to 10 mole equivalents being more preferred. These ranges include all specific values and subranges therebetween, including 3, 5, 7, 10 and 15 mole equivalents.

The alkali metal and the compound forming an organic complex therewith may be added to the reaction system separately. Alternatively, it is possible to form an organic metal complex in advance from them and then add the resulting organic metal complex to the reaction system. For example, when sodium and naphthalene are used, a solidified sodium-naphthalene complex can be prepared by, for example, dispersing metal sodium in molten naphthalene.

The present process may be conducted in the presence or absence of a solvent, but reaction in the presence of a solvent is preferred. Preferred examples of the solvent include ether solvents such as diethyl ether, tetrahydrofuran, dimethoxyethane and diglyme. Among them, tetrahydrofuran is preferred. The solvent is preferably used in an amount falling within a range of 2 to 50 times the weight of Compound (2), with a range of 2 to 10 times the weight being more preferred. These ranges include all specific values and subranges therebetween, including 3, 4, 5, 7, 12, 15, 20, 25, 30 and 40 times the weight of Compound (2).

In the reaction of the present invention, a lower alkylamine can be added to the reaction system in order to improve the reaction selectivity for Polyprenol (1), which is the target product. Examples of such a lower alkylamine include monoalkylamines such as butylamine and dialkylamines such as diethylamine and diisopropylamine. The alkyl groups of the amine may contain 1 to 6 carbon atoms. Among them, diethylamine is preferred. The lower alkylamine is preferably used in an amount falling within a range of 1 to 10 mole equivalents based on Compound (2), with a range of 2 to 4 mole equivalents being more preferred.

It is generally proper to effect the reaction at a temperature ranging from −50 to 50° C., preferably −30 to 0° C. These temperature ranges include all specific values and subranges therebetween, including −40, −20, −10, 5, 10, 20, 30 and 40° C.

After the completion of the reaction, Polyprenol (1) may be isolated from the reaction mixture using well-known methods. For example, Polyprenol (1) is isolated by pouring the reaction mixture in water, extracting with a solvent, for example, a hydrocarbon such as n-hexane or toluene, or an ether such as diisopropyl ether, and then distilling off the solvent from the resulting extract.

When Polyprenol (1) having as R a hydroxyl protecting group is prepared by the process of the present invention, another Polyprenol (1) having as R a hydrogen atom can be obtained by subsequent deprotection. When Polyprenol (1) having as R a hydrogen atom is prepared, on the other hand, another Polyprenol (1) having as R a hydroxyl protecting group can be obtained by protecting the hydroxyl group. Protection or deprotection of the hydroxyl group is conducted using well-known procedures.

Polyprenol (1) obtained above may be purified by distillation, chromatography on a silica gel or the like means.

Compound (2) can be prepared by halogenating an allyl alcohol represented by the following formula (3):

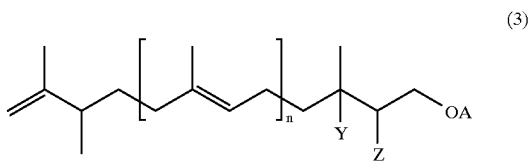

(3)

where Y, Z, A and n have the same meanings as defined above, with thionyl chloride, phosphorus trichloride or phosphorus tribromide in the presence of an ether solvent such as diisopropyl ether (see U.S. Pat. No. 5,714,645, incorporated herein by reference).

The polyprenol prepared by the present process may be formulated into a pharmaceutical composition. Such compositions may be used for preventing or treating diseases caused by immunodeficiency in human beings or animals (see U.S. Pat. No. 4,839,389, incorporated herein by reference). These compositions may be prepared by, for example, combining the polyprenol with a pharmaceutically acceptable carrier. See, for example, U.S. Pat. No. 4,839,389. The pharmaceutical compositions may contain, for example, 0.001 to 99% by weight of the polyprenol, inclusive of all specific values and subranges therebetween.

EXAMPLES

Having generally described this invention, a further understanding can be obtained by reference to certain specific examples which are provided herein for purposes of illustration only and are not intended to be limiting unless otherwise specified.

Referential Example 1

Synthesis of 1-benzyloxy-28-chloro-3,7,11,15,19, 23,27-heptamethyl-6,10,14,18,22,26- octacosahexaene [Compound (2); V=Cl, W and X= carbon-carbon bond, Y=H atom, Z=H atom, A= benzyl group, n=5] and 1-benzyloxy-26-chloro-3,7, 11,15,19,23,27-heptamethyl-6,10,14,18,22,27- octacosahexaene [Compound (2); X=Cl, V and W= carbon-carbon bond, Y=H atom, Z=H atom, A= benzyl group, n=5]

In a 100-ml reaction vessel purged with argon, 8.77 g (14.5 mmol) of 1-benzyloxy-3,7,11,15,19,23,27-heptamethyl-6,10,14,18,22,27-octacosahexaen-26-ol [a compound represented by the formula (3); Y=H atom, Z=H atom, A=benzyl group, n=5] and 0.0106 g (0.145 mmol) of dimethylformamide were charged, followed by the addition of 40 ml of diisopropyl ether to dissolve the former two compounds in the latter. The resulting solution was cooled to −5 to 0° C. To the reaction mixture, 2.76 g (23.2 mmol) of thionyl chloride dissolved in 8 ml of diisopropyl ether were added dropwise at a temperature range of from −5 to 0° C. The reaction was effected at the same temperature for one hour, followed by heating the reaction temperature to room temperature. The reaction was effected at 25° C. for 3 hours.

The reaction mixture was added in portions to 132 g of a 10% aqueous solution of sodium bicarbonate carefully so as not to cause foaming, followed by extraction with diisopropyl ether. The extract was washed with saturated saline and the solvent was distilled off. As a result of analysis of 16.06 g of the residue by liquid chromatography, it contained a mixture of 1-benzyloxy-28-chloro-3,7,11,15,19,23,27-heptamethyl-6,10,14,18,22,26-octacosahexaene and 1-benzyloxy-26-chloro-3,7,11,15,19,23,27-heptamethyl-6, 10,14,18,22,27-octacosahexaene (mixing ratio: primary chloride: secondary chloride=91:9, content of a chloride compound: 56.4 wt. %).

Example 1

Synthesis of 3,7,11,15,19,23,27-heptamethyl-6,10, 14,18,22,26-octacosahexaen-1-ol [Polyprenol (1); Y=H atom, Z=H atom, R=H atom, n=5]

In a 200-ml reaction vessel purged with argon, 8.03 g (content of a chloride compound: 56.4 wt. %, 7.3 mmol) of a mixture (mixing ratio: primary chloride: secondary chloride=91:9) obtained in Referential Example 1, said mixture being composed of 1-benzyloxy-28-chloro-3,7,11, 15,19,23,27-heptamethyl-6,10,14,18,22,26-octacosahexaene and 1-benzyloxy-26-chloro-3,7,11,15,19, 23,27-heptamethyl-6,10,14,18,22,27-octacosahexaene and 5.32 g (41.5 mmol) of naphthalene were charged, followed by the addition of 70 ml of tetrahydrofuran to dissolve the former two compounds in the latter. The resulting solution was cooled to −40 to −30° C. and 2.43 g (33.2 mmol) of diethylamine were added thereto. To the reaction mixture, 0.95 g (41.3 mmol) of sodium metal was added at the same temperature and they were reacted at the same temperature for 3 hours. Then, the reaction was effected further for 3 hours at −20 to −10° C.

The reaction mixture was poured into 100 ml of a saturated aqueous solution of ammonium chloride, followed by extraction with diisopropyl ether. The extract was washed with saturated saline and the organic layer so obtained was analyzed by the internal standard method, whereby 2.69 g of 3,7,11,15,19,23,27-heptamethyl-6,10,1418,22,26-octacosahexane-1-ol were obtained (yield from 1-benzyloxy-3,7,11,15,19,23,27-heptamethyl-6,10,14,18, 22,27-octacosahexaen-26-ol: 74%).

Example 2

Synthesis of 3,7-dimethyl-6-octen-1-ol [Polyprenol (1); Y=H atom, Z=H atom, R=H atom, n=0]

In a 50-ml reaction vessel purged with argon, 0.324 g (content of a chloride compound: 86.6 wt. %, 1.0 mmol) of a mixture (mixing ratio: primary chloride:secondary chloride=70:30) of 1-benzyloxy-8-chloro-3,7-dimethyl-6-octene [Compound (2); V=Cl, W and X=carbon-carbon bond, Y=H atom, Z=H atom, A=benzyl group, n=0] and 1-benzyloxy-6-chloro-3,7-dimethyl-7-octene [Compound (2); X=Cl, V and W=carbon-carbon bond, Y=H atom, Z=H atom, A=benzyl group, n=0] and 0.4 g (3.1 mmol) of naphthalene were charged, followed by the addition of 10 ml of tetrahydrofuran to dissolve the former two compounds in the latter. The resulting solution was cooled to −40 to −30° C. and 0.076 g (1.0 mmol) of diethylamine was added thereto. To the reaction mixture, 0.096 g (4.2 mmol) of sodium metal was added at the same temperature and they were reacted at the same temperature for 3 hours. Then the reaction mixture was reacted further for 3 hours at −20 to −10° C.

The reaction mixture was poured into 10 ml of a saturated aqueous solution of ammonium chloride, followed by extraction with diisopropyl ether. The extract was washed with saturated saline and the organic layer so obtained was analyzed by the internal standard method, whereby 0.109 g of 3,7-dimethyl-6-octen-1-ol was obtained (yield: 70%).

Example 3

Synthesis of 3,7-dimethyl-6-octen-1-ol

In a 50-ml reaction vessel purged with argon, 0.68 g (content of a chloride compound: 82.5 wt. %, 2.0 mmol) of 1-benzyloxy-6-chloro-3,7-dimethyl-7-octene and 0.769 g (6.0 mmol) of naphthalene were charged, followed by the addition of 10 ml of tetrahydrofuran to dissolve the former two compounds in the latter. The resulting solution was cooled to −40 to −30° C. and 0.146 g (2.0 mmol) of diethylamine was added thereto. To the reaction mixture, 0.184 g (8.0 mmol) of sodium metal was added at the same temperature and they were reacted at the same temperature for 3 hours. Then the reaction was effected further for 3 hours at −20 to −10° C.

The reaction mixture was poured into 10 ml of a saturated aqueous solution of ammonium chloride, followed by extraction with diisopropyl ether. The extract was washed with saturated saline and the organic layer so obtained was analyzed by the internal standard method, whereby 0.231 g of 3,7-dimethyl-6-octen-1-ol was obtained (yield: 74%).

Example 4

Synthesis of 3,7,11,15,19,23,27-heptamethyl-6,10, 14,18,22,26-octacosahexaen-1-ol [Polyprenol (1); Y=H atom, Z=H atom, R=H atom, n=5]

In a 100-ml reaction vessel purged with argon, 2.30 g (content of a chloride compound: 64.8 wt.%, 2.4 mmol) of a mixture (mixing ratio: primary chloride:secondary chloride=91:9) of 1-benzyloxy-28-chloro-3,7,11,15,19,23, 27-heptamethyl-6,10,14,18,22,26-octacosahexaene and 1-benzyloxy-26-chloro-3,7,11,15,19,23,27-heptamethyl-6, 10,14,18,22,27-octacosahexaene and 1.79 g (14.0 mmol) of naphthalene were charged, followed by the addition of 30 ml of tetrahydrofuran to dissolve the former two compounds in the latter. The resulting solution was cooled to −40 to −30° C. and 0.77 g (11.0 mmol) of diethylamine were added thereto. To the reaction mixture, 0.10 g (14.0 mmol) of lithium metal was added at the same temperature and they were reacted at the same temperature for 3 hours. Then, the reaction was effected further for 3 hours at −20 to −10° C.

The reaction mixture was poured into 10 ml of a saturated aqueous solution of ammonium chloride, followed by extraction with diisopropyl ether. The extract was washed with saturated saline and the organic layer so obtained was analyzed by the internal standard method, whereby 1.00 g of 3,7,11,15,19,23,27-heptamethyl-6,10,14,18,22,26-octacosahexaen-1-ol were obtained (yield from 1-benzyloxy-3,7,11,15,19,23,27-heptamethyl-6,10,14,18, 22,27-octacosahexaen-26-ol: 84%).

Example 5

Synthesis of 3,7,11,15,19,23,27-heptamethyl-6,10, 14,18,22,26-octacosahexaen-1-ol [Polyprenol (1); Y=H atom, Z=H atom, R=H atom, n=5]

In a 100-ml reaction vessel purged with argon, 2.30 g (content of a chloride compound: 64.8 wt. %, 2.4 mmol) of a mixture (mixing ratio: primary chloride:secondary chloride=91:9) of 1-benzyloxy-28-chloro-3,7,11,15,19,23, 27-heptamethyl-6,10,14,18,22,26-octacosahexaene and 1-benzyloxy-26-chloro-3,7,11,15,19,23,27-heptamethyl-6, 10,14,18,22,27-octacosahexaene and 4.32 g (28.0 mmol) of biphenyl were charged, followed by the addition of 50 ml of tetrahydrofuran to dissolve the former two compounds in the latter. The resulting solution was cooled to −40 to −30° C. and 0.77 g (10.5 mmol) of diethylamine were added thereto. To the reaction mixture, 0.65 g (28.3 mmol) of sodium metal was added at the same temperature and they were reacted at the same temperature for 3 hours. Then, the reaction was effected further for 3 hours at −20 to −10° C.

The reaction mixture was poured into 100 ml of a saturated aqueous solution of ammonium chloride, followed by extraction with diisopropyl ether. The extract was washed with saturated saline and the organic layer so obtained was analyzed by the internal standard method, whereby 0.92 g of 3,7,11,15,19,23,27-heptamethyl-6,10,14,18,22,26-octacosahexaen-1-ol were obtained (yield from 1-benzyloxy-3,7,11,15,19,23,27-heptamethyl-6,10,14,18, 22,27-octacosahexaen-26-ol: 77%).

Obviously, additional modifications and variations of the present invention are possible in light of the above teachings. It is therefore to be understood that within the scope of the appended claims, the invention may be practiced otherwise than as specifically described herein.

Japanese Patent Application No. 108687/1997, filed Apr. 25, 1997, is incorporated herein by reference in its entirety.

What is claimed as new and is desired to be secured by Letters Patent of the United States is:

1. A process for preparing a polyprenol represented by formula (1):

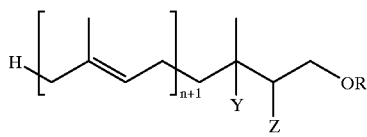

(1)

wherein

Y and Z are each a hydrogen atom, or Y and Z, together, form a carbon-carbon bond, R is a hydrogen atom or a protective group for a hydroxyl group, and n is 0 or an integer not less than 1, comprising:

reacting a complex of an alkali metal and a polycyclic aromatic compound having 10 to 20 carbon atoms with a compound represented by formula (2):

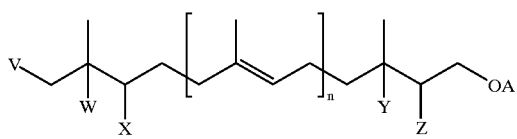

(2)

wherein

Y, Z, and n are as defined above,

A is a protective group for a hydroxyl group, and either

V is a halogen atom, and W and X, together, form a carbon-carbon bond, or

X is a halogen atom, and V and W, together, form a carbon-carbon bond.

2. The process of claim 1, wherein the alkali metal is sodium or lithium.

3. The process of claim 1, wherein the alkali metal is sodium or lithium and the polycyclic aromatic compound is selected from the group consisting of naphthalene, methyl naphthalene, anthracene and biphenyl.

4. The process of claim 1, which is conducted in the presence of an ether solvent.

5. The process of claim 1, which is conducted in the presence of a lower alkylamine.

6. The process of claim 5, wherein the alkyl groups of the alkylamine have 1 to 6 carbon atoms.

7. The process of claim 1, wherein A is a protective group for a hydroxyl group selected from the group consisting of acyl groups, 1-alkoxyalkyl groups, aralkyl groups and tri-substituted silyl groups.

8. The process of claim 7, wherein A is a protective group for a hydroxyl group selected from the group consisting of acetyl, butyryl, benzoyl, p-methoxybenzoyl, methoxymethyl, 1-ethoxyethyl, tetrahydropyranyl, benzyl, p-methoxybenzyl, and trimethylsilyl.

9. The process of claim 1, wherein V is the halogen atom, and W and X, together, form the carbon-carbon bond.

10. The process of claim 9, wherein V is a chlorine, bromine or iodine atom.

11. The process of claim 1, wherein X is the halogen atom, and V and W, together, form the carbon-carbon bond.

12. The process of claim 11, wherein X is a chlorine, bromine or iodine atom.

13. The process of claim 1, wherein n is 0, 1, 2, 3, 4, 5, 6 or 7.

14. The process of claim 1, wherein R is a hydrogen atom.

15. A method of preparing a pharmaceutical composition, comprising preparing a polyprenol according to claim 1, and further comprising combining the polyprenol with a pharmaceutically acceptable carrier.

16. The process of claim 1, wherein polycyclic aromatic compound is a polycyclic aromatic hydrocarbon.

17. The process of claim 1, wherein the polycyclic aromatic compound is selected from the group consisting of naphthalene, methyl naphthalene, anthracene and biphenyl.

* * * * *